(12) United States Patent
Bacher et al.

(10) Patent No.: US 10,610,409 B2
(45) Date of Patent: Apr. 7, 2020

(54) SYSTEM AND METHOD FOR MONITORING PHOTOTOXICITY DURING OPHTHALMIC SURGERY

(71) Applicant: Novartis AG, Basel (CH)

(72) Inventors: Gerald David Bacher, Carlsbad, CA (US); Mark David Labelle, Mattoon, IL (US)

(73) Assignee: Alcon Inc., Rue Louis-d'affry, Fribourg (CH)

( * ) Notice: Subject to any disclaimer, the term of this patent is extended or adjusted under 35 U.S.C. 154(b) by 137 days.

(21) Appl. No.: 15/820,824

(22) Filed: Nov. 22, 2017

(65) Prior Publication Data

US 2018/0147087 A1 May 31, 2018

Related U.S. Application Data

(60) Provisional application No. 62/428,414, filed on Nov. 30, 2016.

(51) Int. Cl.
*A61B 3/10* (2006.01)
*A61B 3/02* (2006.01)
(Continued)

(52) U.S. Cl.
CPC ............ *A61F 9/008* (2013.01); *A61B 3/0008* (2013.01); *A61B 3/0016* (2013.01); *A61B 3/12* (2013.01);
(Continued)

(58) Field of Classification Search
CPC ... A61B 2090/306; A61B 3/0008; A61B 3/13; A61B 90/04; A61B 90/30; A61B 3/0016; A61B 3/12; A61B 18/22; A61B 2017/00154; A61B 2018/2025; A61B 3/14; A61B 90/361; A61B 2090/049; A61B 2090/3612; A61B 90/20; A61B 17/0231; A61B 1/0661; A61B 46/00; A61B 1/0669; A61B 1/07; A61B 2090/3614; A61B 90/36; A61B 1/042
(Continued)

(56) References Cited

U.S. PATENT DOCUMENTS 9,386,918 B2 7/2016 Ammari et al.
2010/0253912 A1 10/2010 Sander
(Continued)

FOREIGN PATENT DOCUMENTS

EP 2937035 A1 10/2015

*Primary Examiner* — Brandi N Thomas

(57) ABSTRACT

The present disclosure provides a system and method for monitoring phototoxicity caused by vitreous visualization device ("VVD") illumination during ophthalmic surgery. The systems and methods determine the cumulative amount of optical energy incident on the retina, which corresponds to phototoxicity, the distance between a cutter of the VVD and the retina, and areas where the vitreous has been removed, or any combination thereof. The disclosure further provides a method for monitoring and preventing phototoxicity caused by VVD illumination during ophthalmic surgery. The method may further include determining the distance between a cutter of the VVD and the retina, and determining areas where the vitreous has been removed based on focus areas of the retina that the plurality of light spots has contacted.

15 Claims, 6 Drawing Sheets

(51) Int. Cl.
  *A61F 9/008* (2006.01)
  *A61B 3/12* (2006.01)
  *A61B 90/00* (2016.01)
  *A61B 3/00* (2006.01)
  A61B 3/13 (2006.01)
  A61B 90/30 (2016.01)
  G02B 26/00 (2006.01)

(52) U.S. Cl.
  CPC ............. *A61B 90/04* (2016.02); *A61B 3/13* (2013.01); *A61B 2090/306* (2016.02); *A61F 2009/00874* (2013.01); *A61F 2009/00878* (2013.01); *G02B 26/00* (2013.01)

(58) Field of Classification Search
  USPC ........ 351/200, 205, 206, 209–211, 221, 222, 351/243–246
  See application file for complete search history.

(56) References Cited

U.S. PATENT DOCUMENTS

2011/0292344 A1   12/2011  Papac et al.
2017/0231711 A1*  8/2017   Abt ..................... A61B 90/361
                                                351/206

* cited by examiner

SYSTEM AND METHOD FOR MONITORING PHOTOTOXICITY DURING OPHTHALMIC SURGERY

TECHNICAL FIELD

The present disclosure relates to ophthalmic surgery and surgical equipment, and more specifically, to systems and methods for monitoring phototoxicity caused by vitreous visualization device ("VVD") illumination.

BACKGROUND

Ophthalmic surgery saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Ophthalmic surgery is surgery performed on the eye or any part of the eye. Ophthalmic surgery is regularly performed to repair retinal defects, repair eye muscles, remove cataracts or cancer, or to restore or improve vision. Certain surgical procedures, for example repairing a retinal detachment, may require a vitrectomy before subsequent procedures may be performed. A vitrectomy is a surgical procedure in which the vitreous is removed from the eye. The vitreous is a clear gel-like substance that holds the retina in place. In certain surgical procedures, the surgeon may need to remove the vitreous to allow access to the retina or other internal structures. In such procedures, the vitreous may be cut and aspirated out of the eye in a procedure called a vitrectomy.

In a vitrectomy, the surgeon inserts small surgical instruments into the eye. Such instruments often include a cutting instrument, a general light source, and an infusion cannula. The cutting instrument may be a vitreous visualization device (VVD), which includes a vitreous cutter and an aspirator to remove portions of the vitreous that have been cut. The VVD may be connected to an optical fiber. The optical fiber propagates an intense illumination beam, generated by an intense light source, called the VVD light source, which is often a laser. This light source provides direct illumination to the vitreous cutter, so that the cutter may be precisely operated in the clear vitreous. The general light source provides basic illumination in the eye that is a significantly lower intensity in comparison to the illumination beam generated by the VVD light source. The infusion cannula is a thin tube that is used to administer water, oil, or a gas to the eye, to replace the vitreous aspirated. This infusion allows the eye to maintain its volume during the procedure so that it does not collapse or become deformed. When performing a vitrectomy, it is important to monitor the patient's risk of phototoxicity caused by light sources used in surgery.

SUMMARY

The present disclosure provides a system for monitoring phototoxicity during ophthalmic surgery. The system includes a vitreous visualization device connected to an optical fiber operable to propagate an illumination beam, the illumination beam creating a light spot on a retina, a surgical microscope, a digital camera operable to detect the light spot and generate data relating to the light spot, and a processor operable to receive data from the digital camera relating to the light spot, the data including a size of the light spot and an elapsed time the light spot has been focused on a focus area of the retina, determine an amount of optical energy incident on the focus area, the amount of optical energy corresponding to the elapsed time, determine a cumulative amount of optical energy incident on the retina, based on the amounts of optical energy incident on a plurality of focus areas, determine whether the cumulative amount of optical energy meets or exceeds a warning threshold, defined in relation to a maximum exposure limit for phototoxicity, generate a warning when the cumulative amount of optical energy meets or exceeds the warning threshold, and transmit the warning to a warning system.

In additional embodiments, which may be combined with one another unless clearly exclusive: the system further comprises a control device connected to the vitreous visualization device, the control device operable to adjust an intensity of the illumination beam, and wherein the processor is further configured to generate and transmit a control signal to the control device, the control signal operable to pause or turn off the illumination beam, when a warning is generated; the system further comprises a control device connected to the vitreous visualization device, the control device operable to adjust an intensity of the illumination beam, and wherein the processor is further configured to generate and transmit a control signal to the control device, the control signal operable to adjust an intensity of the illumination beam, when a warning is generated; the processor is further configured to require receipt of a manual confirmation input before adjusting the intensity of the illumination beam; the system further comprises a device for manual confirmation, the device for manual confirmation operable to input a confirmation of an adjustment of intensity of the illumination beam; the device for manual confirmation of an adjustment is a button, a switch, a key or a joystick, or any combination thereof; the warning system comprises a display operable to present a pictorial representation, and wherein the processor is further configured to generate the pictorial representation to indicate the warning generated, when a warning is generated; the pictorial representation further indicates a cumulative amount of optical energy incident on each focus area of the retina; the pictorial representation further indicates an increase in optical energy incident on each focus area of the retina; the processor is further configured to determine the distance between a cutter on the vitreous visualization device and the retina, the distance determined in relation to the size of the light spot on the retina; the processor is further configured to determine whether the distance between the cutter and the retina meets or exceeds a distance threshold; the processor is further configured to generate a warning when the distance meets or exceeds a distance threshold; the pictorial representation further indicates a change in the size of the light spot, the change corresponding to a new distance between the cutter and the retina; the processor is further configured to determine focus areas of the retina that the light spot has contacted, and generate data relating to focus areas that the light spot has contacted, the focus areas indicating that areas where the vitreous has been removed; and the pictorial representation further indicates areas where the vitreous has been removed.

The present disclosure further provides a method for monitoring phototoxicity during ophthalmic surgery. The method includes receiving data for each of a plurality of light spots created by an illumination beam, the data including a size of a light spot of the plurality and an elapsed time the light spot has been focused on a focus area of the retina, determining an amount of optical energy incident on the focus area in relation to the corresponding elapsed time, determining a cumulative amount of optical energy incident on the retina, based on the amounts of optical energy incident on a plurality of focus areas, determining whether the cumulative amount of optical energy incident on the retina meets or exceeds a warning threshold, defined in relation to a maximum exposure limit for phototoxicity, generating a warning when the cumulative amount of optical energy incident on the retina meets or exceeds the warning threshold, and transmitting the warning to a warning system.

In additional embodiments, which may be combined with one another unless clearly exclusive: the method further comprises generating and transmitting a control signal when a warning is generated, the control signal operable to pause or turn off the illumination beam; the method further comprises generating and transmitting a control signal when a warning is generated, the control signal operable to adjust an intensity of the illumination beam; the method further comprises determining whether manual confirmation is required to transmit the control signal, and only transmitting the control signal after manual confirmation is received; the method further comprises generating a pictorial representation and transmitting the pictorial representation to the warning system; generating the pictorial representation further comprises generating the pictorial representation to indicate the warning generated, when a warning is generated; the method further comprises determining the distance between a cutter of the vitreous visualization device and the retina, the distance determined in relation to the size of the light spot on the retina; the method further comprises determining whether the distance between the cutter and the retina meets or exceeds a distance threshold; the method further comprises generating a warning when the distance meets or exceeds a distance threshold; and the method further comprises determining focus areas of the retina that the light spot has contacted during a surgical procedure, and generating data relating to focus areas the light spot has contacted, the focus areas indicating areas where the vitreous has been removed.

The above systems may be used with the above methods and vice versa. In addition, any system described herein may be used with any method described herein and vice versa.

BRIEF DESCRIPTION OF THE DRAWINGS

For a more complete understanding of the present invention and its features and advantages, reference is now made to the following description, taken in conjunction with the accompanying drawings, which are not to scale, in which like numerals refer to like features, and in which.

DETAILED DESCRIPTION

Figure 1:
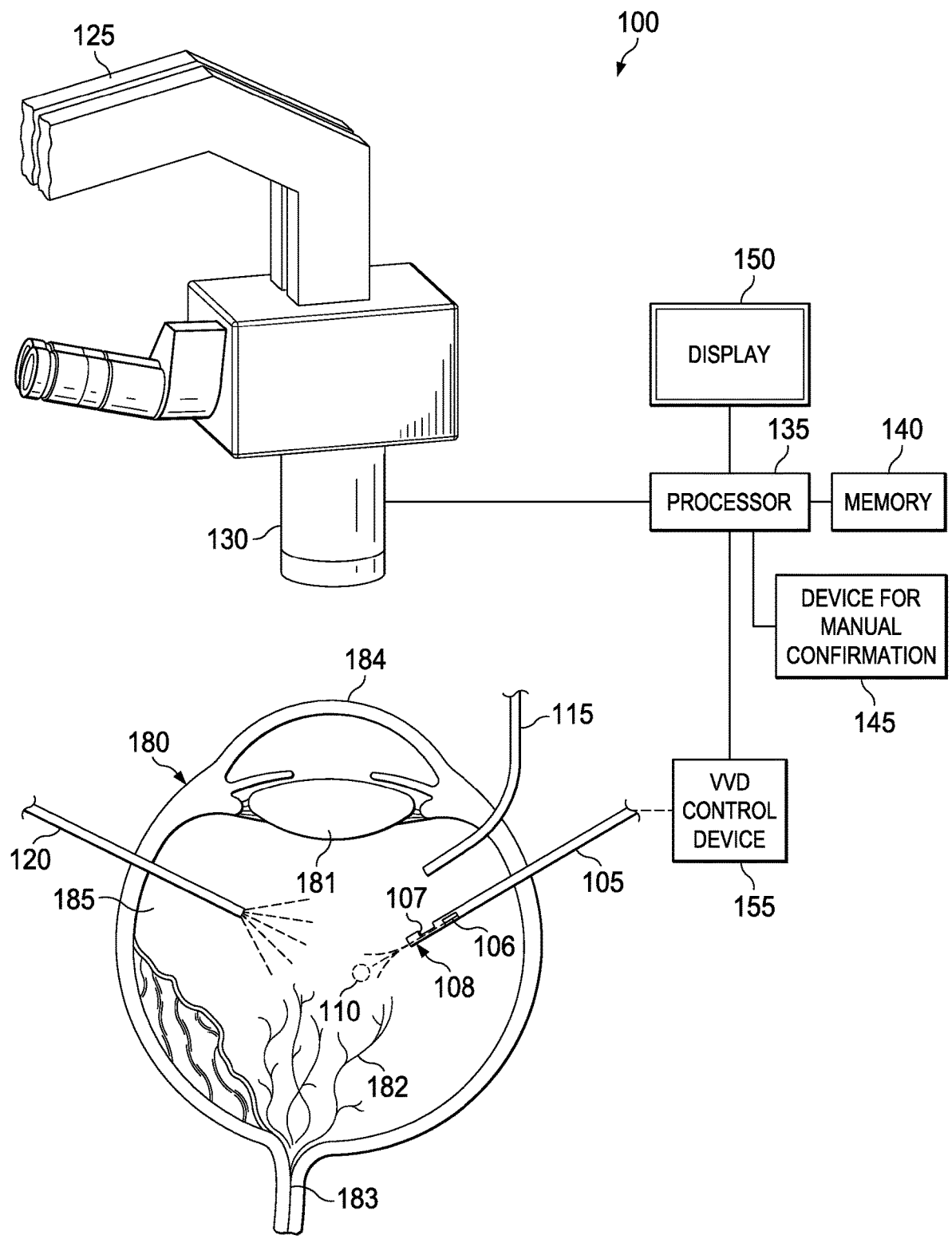
FIG. 1 is a schematic representation of a system for monitoring phototoxicity caused by vitreous visualization device illumination.

In the following description, details are set forth by way of example to facilitate discussion of the disclosed subject matter. It should be apparent to a person of ordinary skill in the field, however, that the disclosed embodiments are exemplary and not exhaustive of all possible embodiments.

The present disclosure provides systems and methods for monitoring phototoxicity caused by vitreous visualization device illumination during ophthalmic surgery. The systems and methods monitor phototoxicity by processing data relating to each of a plurality of light spots created by an illumination beam of a vitreous visualization device ("VVD") to determine: (1) the cumulative amount of optical energy incident on the retina throughout the procedure, and whether the cumulative amount of optical energy is near a maximum exposure limit of phototoxicity; (2) the distance between the retina and the vitreous cutter of the VVD; (3) and areas from which the vitreous has been removed, based on focus areas the illumination beam has contacted during the procedure.

In ophthalmic surgery, the surgeon may need to access structures toward the back of the eye (the area generally behind the lens), such as the retina. The retina is a thin layer of tissue at the back of the eye that contains photoreceptor cells sensitive to light. These cells trigger nerve impulses that pass to the brain through the optic nerve. Generally, the retina receives light that the lens has focused and converts the light into a neural signal that is sent to the brain, allowing for visual recognition. The vitreous is a clear gel-like substance that fills the space between the lens (toward the front of the eye) and the retina (toward the back of the eye). The vitreous does not contain any blood vessels and is mostly composed of water, making it transparent and colorless. The vitreous is attached directly to the retina, with the strongest attachment in the peripheral regions, near the vitreous base. Because the vitreous occupies the space between the lens and the retina, in certain surgical procedures, the surgeon may need to cut and remove it to gain access. A vitrectomy is a procedure in which some or all of the vitreous is removed from the eye.

In a typical vitrectomy, general anesthesia is administered to the patient or local anesthesia is applied to the operative eye, and an eyelid speculum is placed to hold the eye open throughout the procedure. The surgeon may then insert surgical instruments into the eye. Such instruments often include a VVD, a general light source, and an infusion cannula. The VVD may be, for example, a standard pneumatic guillotine vitreous cutter with an optical fiber added to it. The optical fiber propagates an intense illumination beam, the light of which is generated by the VVD light source. The optical fiber also directs the beam of light across and slightly above the cutter port. For example, the optical fiber may be coupled to a supercontinuum laser that is able to provide enough white light through a 25 µm core fiber to adequately illuminate the vitreous; however, any source bright enough to provide adequate illumination through the optical fiber would be effective.

The optical fiber that is attached to the vitreous cutter is generally not a part of the laser, although certain lasers may incorporate an optical fiber. For example, when a supercontinuum laser is used as the VVD light source, the laser incorporates a photonic crystal fiber that is not directly connected to the vitreous cutter. In contrast, the optical fiber typically extends from an illumination console and is directly connected to the vitreous cutter.

Because the vitreous is made of approximately 1% collagen and 99% water, it is not readily observed using visible light. To allow the user to observe the vitreous, the optical fiber propagates the intense illumination beam across the field of view. A small amount of light will scatter off of the collagen/water interfaces and be directed to the surgical microscope and a digital camera. This illumination beam exerts a significant amount of optical energy on the eye. In most procedures, the user almost constantly moves the vitreous cutter and rarely holds it stationary, so the risk of phototoxicity caused by the illumination beam is low. However, the user may become fixated on an area and may inadvertently hold the vitreous cutter at a stationary position with the illumination beam directed at that area, or the user may have difficulty distinguishing areas where the vitreous has been removed as opposed to areas where the vitreous remains, causing the user to direct the beam over the same area multiple times. In such situations, the risk of phototoxicity increases.

Generally, there are two types of phototoxicity caused by VVD illumination, both of which can damage the light sensitive cells of the retina: (1) total illumination thermal hazard, which is caused by a rise in temperature directly related to the cumulative amount of optical energy incident on the retina; and (2) aphakic hazard, which is direct photochemical damage produced by wavelengths in the UV and blue portions of the light spectrum.

Total illumination thermal hazard relates to the cumulative amount of optical energy incident on the retina, per unit area. Optical energy causes the temperature inside the eye to rise. If the optical power is high enough, the energy will be deposited faster than the thermal diffusion processes in the eye can dissipate it, causing the temperature to rise to unsafe levels. This rise in temperature can permanently damage the retina and other internal structures of the eye. Total illumination thermal hazard may arise in a short time period, for example, within seconds of accumulating optical energy at a light spot.

In contrast, aphakic hazard is direct photochemical damage produced by certain wavelengths of light that are toxic to the eye. These wavelengths of light are generally in the UV to blue portions of the spectrum. Significant toxicity is observed in the UV region around 300 nm, and toxicity declines through UV and blue spectral regions, becoming relatively insignificant around 500 nm. In typical situations, the lens and other structures of the eye filter and protect the retina from such wavelengths. However, in a vitrectomy, the retina is readily exposed to these wavelengths because the VVD is inserted behind the lens and only the clear vitreous separates the illumination beam from the retina.

A maximum exposure limit for aphakic hazard may be determined by measuring the radiometric flux of the optical fiber or laser (spectrum in units of mW/nm). The resulting effective aphakic power is then divided by the luminous flux to define the normalized aphakic power (mW/lumen), which essentially provides a measurement of how dangerous the illumination beam is per unit brightness. ISO standard ISO 15752:2010(E) indicates that photochemical damage effects accrue for a maximum of 30 minutes, so the maximum exposure limit is set to prevent excessive exposure over this timeframe. For example, normalized aphakic hazard has been measured to be 0.52 mw/lumen, which corresponds to roughly 60 seconds of exposure allowable before aphakic hazard occurs, based on an approximately 10-15 lumen illumination beam output from a laser VVD light source.

Referring now to the figures, FIG. 1 is a system 100 for monitoring phototoxicity caused by vitreous visualization device illumination. As shown, system 100 provides a VVD 105 connected to an optical fiber 106 that propagates an intense illumination beam generated by a VVD light source, the illumination beam creating a light spot 110 on retina 182. The VVD also includes a vitreous cutter 108 and an aspirator 107. System 100 also includes a surgical microscope 125, a digital camera 130 that detects a light spot and generates data relating to the light spot, a warning system, and processor 135. The system may further include infusion cannula 115, light source 120, device for manual confirmation 145, and VVD control device 155. Surgical microscope 125 may be any suitable microscope, for example, a light or electron microscope. Surgical microscope 125 may be a standalone microscope or may be integrated into system 100, for example, such that enlarging and focusing components of the surgical microscope are integrated into system 100.

As shown, for a vitrectomy, surgical instruments VVD 105, infusion cannula 115, and light source 120 are inserted into the eye 180. Digital camera 130 detects each of a plurality of light spots created by the VVD and generates data relating to each light spot of the plurality. The data generated may include the size of each light spot, the elapsed time that each light spot has been focused on a focus area of the retina, and focus areas of the retina that each light spot has contacted.

To monitor phototoxicity, processor 135 receives this data from the digital camera, and determines an amount of optical energy incident on the focus area of the retina. Because the illumination beam is operated at a known intensity, the amount of optical energy incident on the focus area may be determined in relation to the elapsed time the beam has been focused on the focus area at that level of intensity. The processor then determines the cumulative amount of optical energy incident on the retina, based on the amounts of optical energy incident on a plurality of focus areas. The cumulative amount of optical energy incident on the retina may be determined as the sum of the amounts of optical energy incident on the retina from each light spot of the plurality. The processor then determines whether the cumulative amount of optical energy meets or exceeds a warning threshold, and generates a warning when the cumulative amount of optical energy meets or exceeds the warning threshold. The processor may then transmit the warning to a warning system.

The warning system may include a display and the processor may also generate a pictorial representation and transmit the pictorial representation, for example, to display 150. Display 150 may include multiple displays and may be a screen, a heads-up display, or a combination. Alternatively, the warning generated may be transmitted to a warning system that does not include a display, and without generating a pictorial representation that includes the warning when a warning is generated. The warning system may include a speaker, light indicator, haptic feedback device, or other device that indicates to the user that a warning was generated.

Processor 135 may be further configured to determine aphakic hazard by reference to reference spectrum because the spectrum of the VVD light source generally does not vary excessively over time. The processor may also be configured to account for implementation of aphakic hazard mitigating measures, such as including known spectral filters into the illumination console to reduce the aphakic hazard in longer procedures.

A warning threshold is defined in relation to a maximum exposure limit for phototoxicity. Each warning threshold may be defined by a user and one or multiple warning thresholds may be used. For example, warning thresholds may be defined as 50%, 75%, and 90% of the maximum exposure limit, or 50%, 25%, and 10% of additional exposure is permissible before the maximum exposure limit is reached. Warning thresholds may also be defined as measurements of exposure that correlate to a percentage of a maximum exposure limit. For example, if the maximum exposure limit for aphakic hazard is 0.52 mw/lumen, then a warning threshold may be defined at 0.45 mw/lumen. Alternatively, because the illumination beam is operated at a known level of intensity, the amount of optical energy incident on the retina may be determined in relation to elapsed time the illumination beam has been focused during the procedure. Thus, warning thresholds and the maximum exposure limit may be defined in relation to such elapsed time. For example, at maximum intensity, a warning threshold may be defined at 45 seconds, with the maximum exposure limit for aphakic hazard defined at 60 seconds of exposure.

Any warning described herein may be, for example, in the form of a colored light, a blinking light, a flashing light, a sound, an alarm, a whistle, a graphic, or any other signal that indicates to the user that that a warning was generated. The warning may be presented to the user in real time, preferably as soon as it is determined that a warning is required. Real time may mean in less than half a second, in less than one second, or otherwise in less than the normal reaction time of a user based on visual information.

System 100 may further include VVD control device 155, and processor 135 may be further configured to generate a control signal to pause, turn off, or adjust the intensity of the illumination beam, when a warning threshold has been met or exceeded. The control signal is transmitted to VVD control device 155 and can help prevent further damage due to phototoxicity by pausing, turning off, or adjusting the intensity of the illumination beam. System 100 may further include device for manual confirmation 145, which may be used to input a manual confirmation of a control signal, and the processor may be further configured to require manual confirmation before generating or transmitting a control signal. If manual confirmation is not required, the system may be configured to automatically pause, turn off, or adjust the intensity of the illumination beam when a warning threshold is met. In the event the illumination beam is automatically paused or turned off, a warning included in the pictorial representation may indicate to the user that the illumination beam has been paused or turned off. In the event the intensity of the illumination beam is adjusted, another warning may indicate to the user that the adjustment has been performed. If manual confirmation is required, the control signal will not be generated until manual confirmation is received, or a control signal already generated will not be transmitted to the control device until manual confirmation is received. Device for manual confirmation 145 may be a button, a switch, a key, a joystick, or any device that can input a confirmation.

Processor 135 may be further configured to determine the distance between the cutter 108 and the retina 182. Determining the distance between the cutter and the retina assists the user in avoiding accidental contact with the retina. This increased precision may allow the user to shave the vitreous closer to the retina. To determine this distance, processor 135 receives data from the digital camera that includes the size of each light spot of the plurality. The distance between the cutter and the retina may be determined by reference to the size of the light spot on the retina because the light from the illumination beam makes a distinctively shaped, well-defined spot on the retina. Accordingly, the relative size of the light spot will be larger when the distance between the cutter and the retina is greater, and the light spot will be smaller when the distance between the cutter and the retina is lesser.

Also, processor 135 may determine whether the distance between the cutter and the retina meets or exceeds a distance threshold. Distance thresholds may be defined by a user and one or multiple distance thresholds may be used. For example, a distance threshold may be defined as 50%, 75%, and 90% of the distance between the lens and the retina. A distance threshold may also be defined by any unit of measuring distance, such as a millimeter, a micron ($1 \times 10^{-6}$ m), a nanometer ($1 \times 10^{-9}$ m), or a picometer ($1 \times 10^{-12}$ m); for example, 4 microns away from the retina or 2 microns from the back of the lens. If a distance threshold is not met or exceeded, the processor may terminate this process without generating a warning. In contrast, if a distance threshold is met or exceeded, the processor may generate a warning to include in the pictorial representation. The warning informs the user that the cutter is within a potentially dangerous proximity to the retina such that contact with the retina is imminent with additional movement. This warning is useful to inform the surgeon of whether any surgical attachments may be added to the end of the cutter based on the current operating position.

Figure 3:
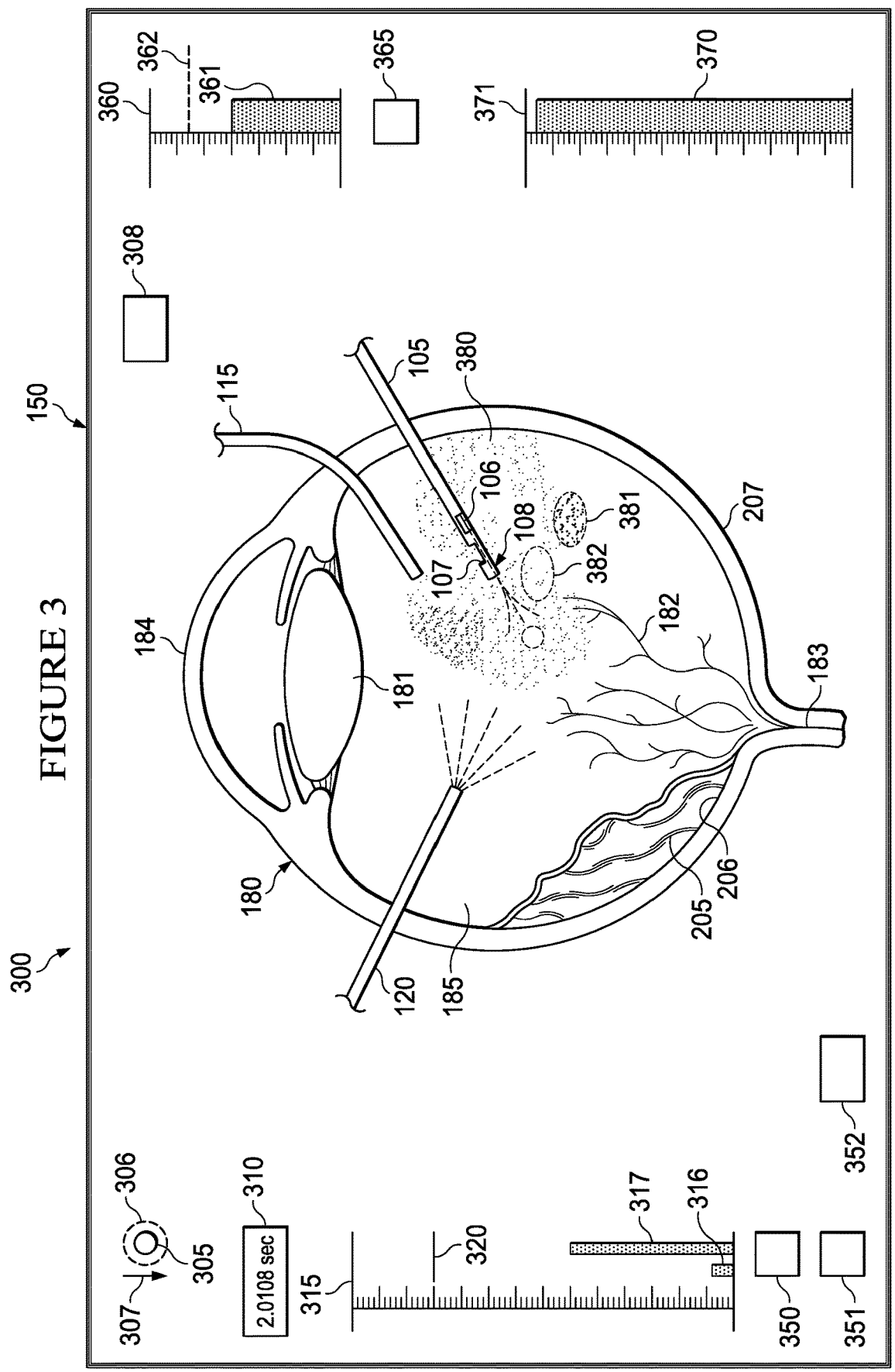
FIG. 3 is a pictorial representation that indicates phototoxicity caused by vitreous visualization device illumination.

System 100 may further be configured to determine areas where the vitreous has been removed based on focus areas contacted by the illumination beam. To determine areas where the vitreous has been removed, processor 135 receives data for each of the plurality of light spots that includes focus areas of the retina contacted by the each of the light spots and elapsed time the illumination beam has been focused on each focus area. These focus areas indicate areas where the vitreous has been removed because each light spot is created by the illumination beam, which passes through the cutter port of the VVD, and thus corresponds to areas where the cutter has cut and aspirated the vitreous. The processor may generate data to include in the pictorial representation indicating areas the vitreous has been removed. FIG. 3 provides an example of a pictorial representation that includes data relating to areas where the vitreous has been removed. Specifically, colored and shaded focus areas 380 indicate areas where the vitreous has been removed. To provide greater detail, focus area 381, for example, is presented as darker than focus area 382. This darker shade or color signifies that the light spot has been focused on focus area 381 for a greater amount of elapsed time as compared to focus area 382, which may indicate to the user that further cutting and aspiration is required at focus area 381 in comparison to focus area 382.

System 100 may determine and generate a pictorial representation that includes any of the following elements individually or in any combination: the cumulative amount of optical energy incident on the retina, the distance between the cutter and the retina, and areas where the vitreous has been removed.

Processor 135 may include, for example a microprocessor, microcontroller, digital signal processor (DSP), application specific integrated circuit (ASIC), or any other digital or analog circuitry configured to interpret and/or execute program instructions and/or process data. In some embodiments, processor 135 may interpret and/or execute program instructions and/or process data stored in a memory. The memory may be configured in part or whole as application memory, system memory, or both. The memory may include any system, device, or apparatus configured to hold and/or house one or more memory modules. Each memory module may include any system, device or apparatus configured to retain program instructions and/or data for a period of time (e.g., computer-readable media). The various servers, electronic devices, or other machines described may contain one or more similar such processors or memories for storing and executing program instructions for carrying out the functionality of the associated machine.

Figure 2:
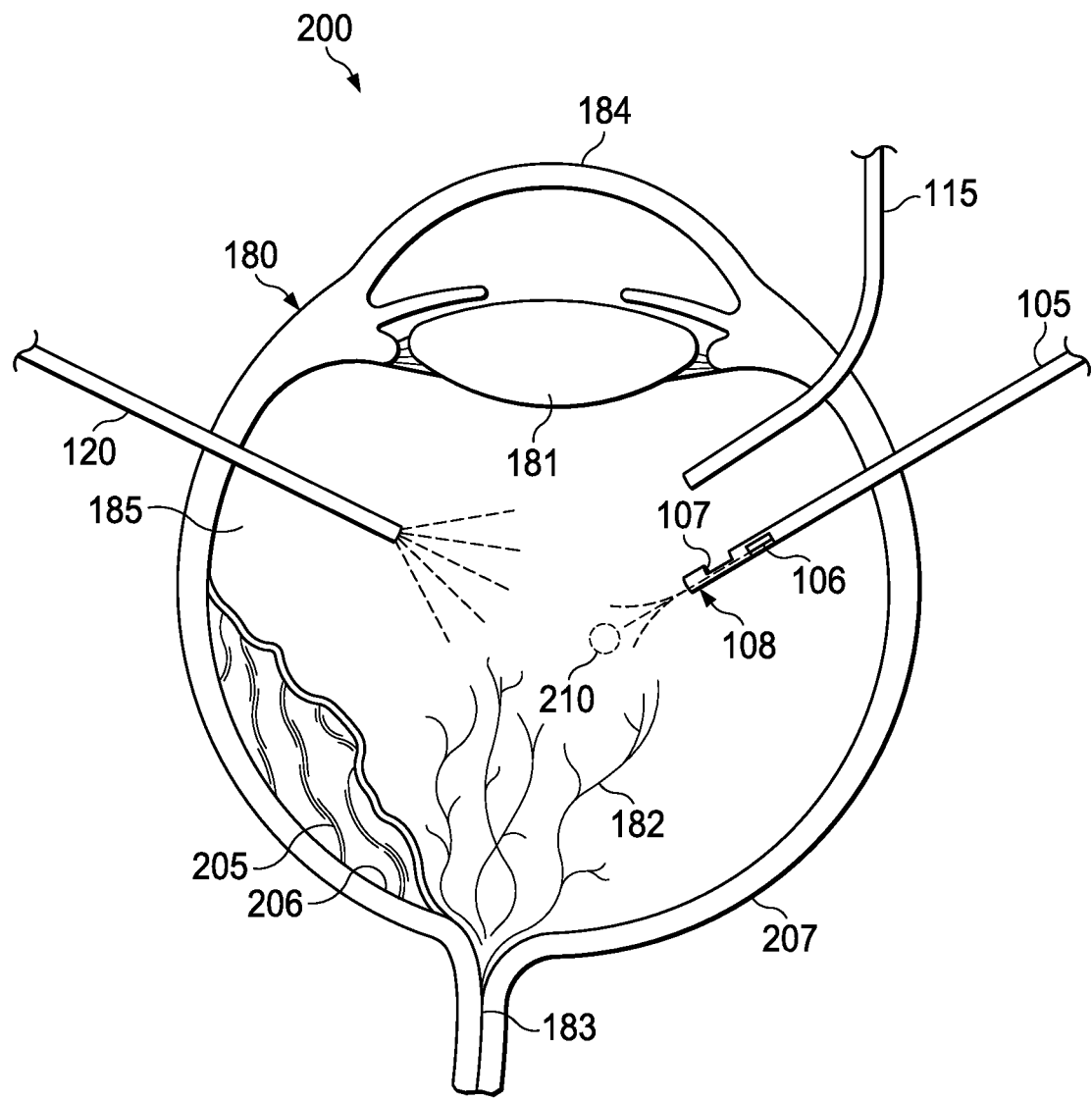
FIG. 2 is a schematic representation of surgical instruments inserted in an eye during a vitrectomy.

FIG. 2 is a schematic representation 200 of surgical instruments inserted in an eye during a vitrectomy. As shown, eye 180 has a detached retina 205, which is toward the back of the eye (opposite the cornea 184 and lens 181). The retina 182 has become detached from choroid 206. To access the retina, the vitreous 185 must be removed. To perform the vitrectomy, general light source 120, infusion cannula 115, and VVD 105 have been inserted into the eye. VVD 105 is connected to an optical fiber 106 that propagates an illumination beam, which creates light spot 210. The VVD also includes aspirator 107 and vitreous cutter 108.

As shown in FIG. 2, light source 120 provides basic illumination inside the eye that is a significantly lower intensity in comparison to the illumination beam propagated by the optical fiber, and generally does not contribute to phototoxicity risk. In contrast, the optical fiber connected to the VVD propagates a high intensity illumination beam that contributes to phototoxicity. The optical fiber propagates the illumination beam across and slightly above the cutter port of the vitreous cutter. Light spot 210, created by the illumination beam, allows the surgeon better visualization of areas where the vitreous has been removed. Light spot 210 is focused on a focus area of the retina, exerting an amount of optical energy incident on the retina. Phototoxicity is directly related to the cumulative amount of optical energy incident on the retina. Phototoxicity may be based on total illumination causing a dangerous temperature change in the eye, or aphakic hazard caused by certain wavelengths of UV light inducing direct photochemical damage in the eye. Because the vitreous is clear, it is difficult to discern places where the vitreous has been removed (further cutting and aspiration is not necessary) from places where the vitreous remains (further cutting and aspiration is necessary).

To perform vitreous removal, the vitreous cutter 108 physically cuts the vitreous, allowing it to be removed via suction by the aspirator 107. As the vitreous is removed from the eye, the internal volume and internal pressure of the eye is in flux, although the infusion line is implemented as part of a feedback loop that attempts to maintain a constant inter-ocular pressure (IOP) during the procedure as vitreous is aspirated. The light from the illumination beam makes a distinctively shaped, well-defined spot on the retina. Accordingly, the light spot created by the illumination beam indicates focus areas where the cutter has been directed and also indicates areas where the vitreous has been removed. In order to prevent the eye from collapsing or becoming deformed by such changes, infusion cannula 115 simultaneously administers water, oil, or a gas to the eye to replace the vitreous aspirated. Once the vitreous has been removed, the surgeon has significantly improved access to the retina and other structures in the back of the eye.

FIG. 3 is a pictorial representation 300 that indicates phototoxicity caused by vitreous visualization device illumination, the pictorial representation presented to a user on display 150. As shown, the pictorial representation presents information related to the size of the light spot on the retina 305, elapsed time the light spot has been focused at the current focus area 310, amount of optical energy incident on the focus area 316, cumulative amount of optical energy incident on the retina 317, phototoxicity warning 350, manual confirmation warning 351, warning of automated adjustment of illumination beam intensity 352, measurement of light spot size 308, distance between the cutter and the retina 360, distance threshold 362, a proximity warning 365, and the intensity of the illumination beam 370.

The pictorial representation includes eye 180, lens 181, detached retina 205, optical nerve 183, vitreous 185. Surgical instruments inserted in the eye include general light source 120, infusion cannula 115, and VVD 105, which includes vitreous cutter 108 and aspirator 107. Optical fiber 106 is connected to VVD 105. Optical fiber 106 propagates the illumination beam that creates a light spot on the retina at each focus area of the beam. Colored and shaded focus areas 380 indicate areas each light spot of a plurality of light spots has contacted, which indicates places the vitreous has been removed. To provide greater detail, focus area 381, for example, is presented as darker than focus area 382. This darker shade signifies that the light spot has been focused on focus area 381 for a greater amount of time as compared to focus area 382, which may indicate to the user that further cutting and aspiration is required at focus area 381 in comparison to focus area 382.

Figure 4:
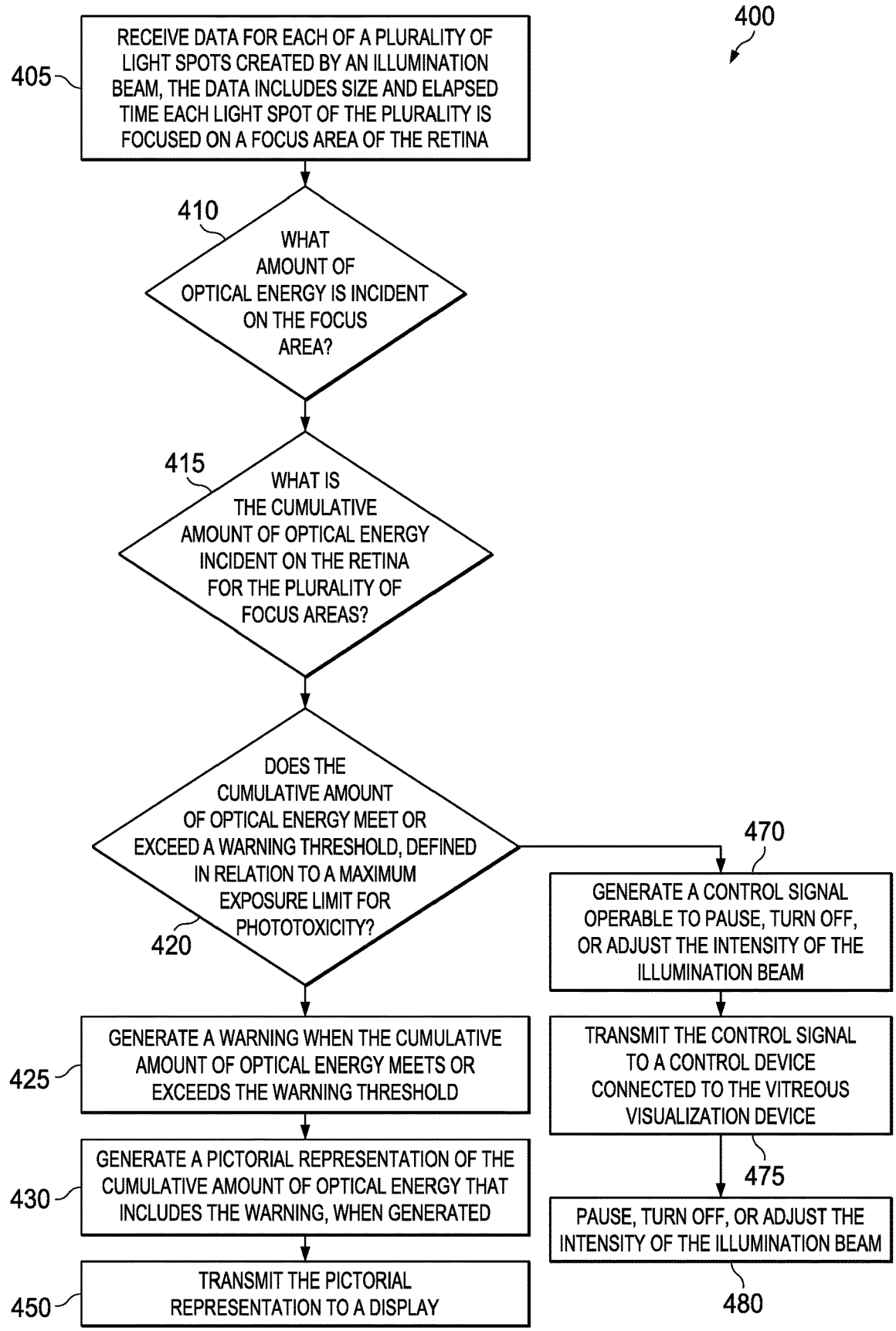
FIG. 4 is a flowchart of a method for monitoring phototoxicity caused by vitreous visualization device illumination.

Pictorial representation 300 may also include a visual representation of the size of the light spot on the retina 305, and a visual representation of the previous size of the light spot on the retina 306. Symbol 307 may indicate the relative change in the size of the light spot, which corresponds to a change in the distance between the cutter and the retina. Elapsed time 310 indicates the amount of time the light spot has been focused on current focus area 311. Phototoxicity meter 315 provides information related to amounts of optical energy incident on the retina, and may include bars 316 and 317. Phototoxicity meter 315 may present such information in any manner, for example, as a scale, a bar graph, a line graph, a fraction of a whole, with a number or a percentage, or by changing size, color, or shade. In this example, phototoxicity meter 315 is presented as a scale with bars 316 and 317. Bar 316 indicates the amount of optical energy incident on current focus area 311. In contrast, bar 317 indicates the cumulative amount of optical energy incident on the retina. As illustrated in FIG. 4, the cumulative amount of optical energy incident on the retina may be determined as the sum of the amounts of optical energy incident on the retina from each light spot of the plurality. As shown, the phototoxicity meter also includes a warning threshold 318, which is defined by the user. In this example, warning threshold 318 indicates a cumulative amount of phototoxicity incident on the retina that is 75% of the maximum limit of exposure for phototoxicity. When this warning threshold is met or exceeded, the pictorial representation may further include warning 350. Such warning, for example, may be in the form of a colored light, a blinking light, a flashing light, a sound, an alarm, a whistle, a graphic, or any other signal that indicates to the user that a warning was generated. The warning may be presented to the user in real time, preferably as soon as it is determined that a warning is required. Real time may mean in less than half a second, in less than one second, or otherwise in less than the normal reaction time of a user based on visual information.

As described in the system of FIG. 1, when a warning threshold has been met or exceeded, a control signal may be generated, the control signal to pause, turn off, or adjust the intensity of the illumination beam generated by the VVD. The system may be configured to automatically pause or turn off the illumination beam when a warning threshold is met. In the event the illumination beam is automatically paused or turned off, warning 352 may indicate to the user that the illumination beam has been paused or turned off. Alternatively, the system may be configured to adjust the intensity of the illumination beam when a warning threshold is met or exceeded. This adjustment may be performed automatically or after manual confirmation has been input, if the system is configured to require manual confirmation of an adjustment. Similarly, the system may be configured to notify the user that manual confirmation is required to pause or turn off the illumination beam. Symbol 351 indicates that manual confirmation is required to adjust, pause or turn off the illumination beam because a warning threshold has been met. Symbol 351 may be a button to provide manual confirmation, for example, if display 150 is a touchscreen display.

Illumination beam intensity meter 372 may indicate the intensity level or power of the illumination beam in any manner, for example, as a scale, a bar graph, a line graph, a fraction of a whole, with a number or a percentage, or by changing size, color, or shade. As shown, meter 372 indicates the illumination beam's intensity with bar 370 and the maximum intensity level of the VVD as line 371. Meter 372 is useful to indicate to the user any change in intensity after a warning threshold has been reached and a control signal has been sent to the VVD to pause, turn off, or adjust the intensity of the illumination beam.

Distance meter 372 may indicate the distance between the cutter of the VVD and the retina in any manner, for example, as a scale, a bar graph, a line graph, a fraction of a whole, with a number or a percentage, or by changing size, color, or shade. As shown, meter 360 indicates the distance between the cutter and the retina with a bar. Also shown is distance threshold 362. Distance thresholds may be defined by a user and one or multiple warning thresholds may be used. For example, warning thresholds may be defined as 50%, 75%, and 90% of the distance between the lens and the retina or the cornea and the retina. In another example, warning thresholds may be defined by any unit of measuring distance, such as a millimeter, a micron ($1\times10^{-6}$ m), a nanometer ($1\times10^{-9}$ m), or a picometer ($1\times10^{-12}$ m). As described in FIG. 5, a proximity warning 365 may be generated when the distance between the cutter and the retina meets or exceeds a threshold distance. Also, numerical measurement of light spot size 308 indicates a the size of light spot 311 (also visually represented at 305).

Any aspect of the pictorial representation described may be presented in any combination. As such, the visual representations, indications, warnings, symbols, and other aspects described may be presented individually or in any combination.

FIG. 4 is a flowchart of a method for monitoring phototoxicity caused by vitreous visualization device illumination. At step 405, data may be received relating to a plurality of light spots created by an illumination beam, the data including the size of each light spot of the plurality and an elapsed time each light spot has been focused on a focus area of the retina. At step 410, the amount of optical energy incident on a focus area of the retina may be determined for a light spot of the plurality. At step 415, the cumulative amount of optical energy incident on the retina may be determined for the plurality of light spots. The cumulative amount of optical energy incident on the retina may be determined as the sum of the amounts of optical energy incident on the retina corresponding to each light spot of the plurality.

At step 420, whether the cumulative amount of optical energy incident on the retina meets or exceeds a warning threshold may be determined. The warning threshold is defined in relation to a maximum exposure limit for phototoxicitiy. Warning thresholds may be defined by a user and one or multiple warning thresholds may be used. For example, warning thresholds may be defined as 50%, 75%, and 90% of the maximum exposure limit or 50%, 25%, and 10% of additional exposure is permissible before the maximum exposure limit is reached. Warning thresholds may also be defined as measurements of exposure that correlate to a percentage of a maximum exposure limit. For example, if the maximum exposure limit for aphakic hazard is 0.52 mw/lumen, then a warning threshold may be defined at 0.45 mw/lumen. Alternatively, because the illumination beam is operated at a known level of intensity, the amount of optical energy incident on the retina may be determined in relation to elapsed time the illumination beam has been focused during the procedure. Thus, warning thresholds and the maximum exposure limit may be defined in relation to such elapsed time. For example, at maximum intensity, a warning threshold may be defined at 45 seconds, with the maximum exposure limit for aphakic hazard defined at 60 seconds of exposure.

At step 425, a warning may be generated when the cumulative amount of optical energy incident on the retina meets or exceeds a warning threshold. The warning informs the user that the retina has been exposed to an amount of optical energy at least equivalent to a warning threshold defined by the user. Such warning, for example, may be in the form of a colored light, a blinking light, a flashing light, a sound, an alarm, a whistle, a graphic, or any other signal that indicates to the user that that a warning was generated. The warning may be presented to the user in real time, preferably as soon as it is determined that a warning is required. Real time may mean in less than half a second, in less than one second, or otherwise in less than the normal reaction time of a user based on visual information.

At step 430, a pictorial representation of the cumulative amount of optical energy incident on the retina may be generated. The pictorial representation may include the warning generated at step 425 when a warning is generated. At step 450, the pictorial representation may be transmitted to a warning system, which may include a display.

Alternatively, the warning generated at step 425 may be transmitted to a warning system that does not include a display. The warning may be generated without generating the pictorial representation (of step 430) that includes the warning. The warning system may instead include a speaker, light indicator, haptic feedback device, or other device that indicates to the user that a warning was generated.

Alternatively, after step 420, a control signal may be generated at step 470, when the cumulative amount of optical energy meets or exceeds the warning threshold. The control signal may be to pause the illumination beam, turn off the illumination beam, or adjust the intensity of the illumination beam. At step 475, the control signal may be transmitted to a control device to pause, turn off, or adjust the intensity of the illumination beam. At step 480, the illumination beam is paused, turned off, or the intensity of the illumination beam is adjusted.

The method may further include a step to determine whether manual confirmation of a control signal is required, and the control signal is only generated or transmitted after a manual confirmation is received. Manual confirmation may be required for any control signal generated or transmitted and may be required for certain warning thresholds and not others, in any combination. In one example, if a manual confirmation is required, the control signal will not be generated until confirmation is received; alternatively, if a manual confirmation is required, the control signal generated will not be transmitted until confirmation is received. In another example, if manual confirmation is not required, a control signal to pause or turn off the illumination beam may be generated and transmitted as soon as the warning threshold is met. In contrast, as another example, if manual confirmation is required, a control signal to adjust the intensity of the illumination beam may be either generated or transmitted only after manual confirmation is received so that the user may complete the current task before the illumination beam intensity is adjusted downward.

Figure 5:
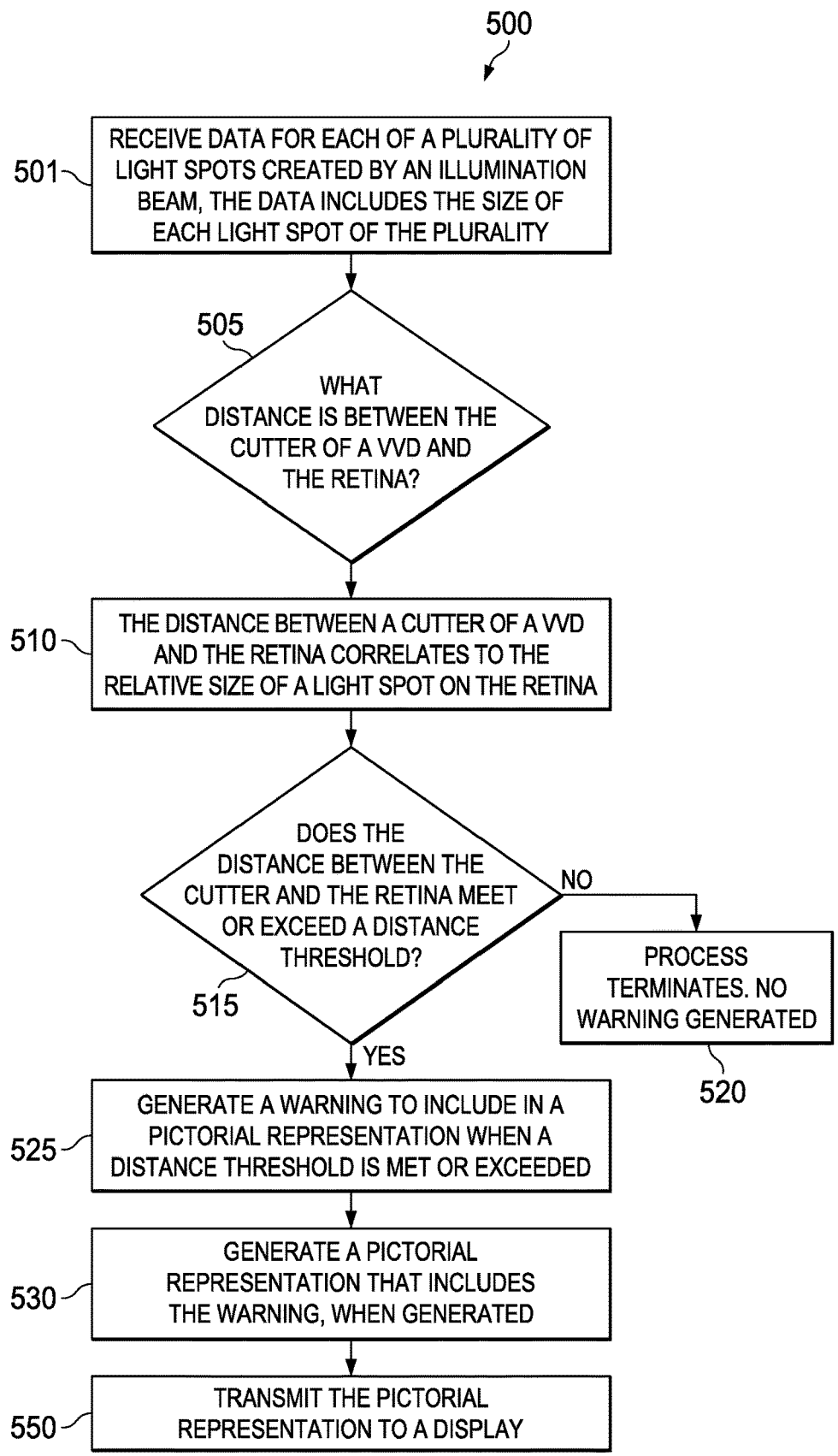
FIG. 5 is a flowchart of a method for determining the distance between a vitreous cutter and the retina.

FIG. 5 is a flowchart of a method for determining the distance between a vitreous cutter and the retina. At step 501, data may be received relating to a plurality of light spots created by an illumination beam, the data including the size of each light spot of the plurality. At step 505, the distance between the cutter and the retina may be determined. As described in 510, the distance between the cutter and the retina may be determined in relation to the size of the light spot on the retina because the illumination beam passes through the cutter port of the VVD, creating the light spot. Accordingly, the relative size of the light spot will be larger when the distance between the cutter and the retina is greater, and the light spot will be smaller when the distance between the cutter and the retina is lesser. At step 515, whether the distance between the cutter and the retina meets or exceeds a distance threshold may be determined. Distance thresholds may be defined by a user and one or multiple distance thresholds may be used. For example, a distance threshold may be defined as 50%, 75%, and 90% of the distance between the lens and the retina. A distance threshold may also be defined by any unit of measuring distance, such as a millimeter, a micron ($1\times10^{-6}$ m), a nanometer ($1\times10^{-9}$ m), or a picometer ($1\times10^{-12}$ m); for example, 4 microns away from the retina.

At step 520, the process terminates and no warning is generated when the distance between the cutter and the retina does not meet or exceed a distance threshold. Alternatively, at step 525, a warning may be generated when a distance threshold is met or exceeded. The warning informs the user that the cutter is within a potentially dangerous proximity to the retina such that contact with the retina is imminent with additional movement. This warning is useful to inform the surgeon of whether any surgical attachments may be added to the end of the cutter based on the current operating position. Such warning, for example, may be in the form of a colored light, a blinking light, a flashing light, a sound, an alarm, a whistle, a graphic, or any other signal that indicates to the user that a warning was generated. The warning may be presented to the user in real time, preferably as soon as it is determined that a warning is required. Real time may mean in less than half a second, in less than one second, or otherwise in less than the normal reaction time of a user based on visual information.

At step 530, a pictorial representation may be generated that includes an indication of the distance between the cutter and the retina, and at step 550, the pictorial representation may be transmitted to a display. The pictorial representation may include the warning generated at step 525 when a warning is generated. FIG. 3 provides an example of a pictorial representation that includes a distance meter 372 that indicates the distance between the cutter and the retina. FIG. 3 also provides proximity warning 365, which indicates that a distance threshold has been met or exceeded, causing a warning to be generated. Alternatively, the warning generated at step 525 may be transmitted to a warning system that does not include a display. The warning may be generated without generating the pictorial representation (of step 530) that includes the warning. The warning system may instead include a speaker, light indicator, haptic feedback device, or other device that indicates to the user that a warning was generated.

Figure 6:
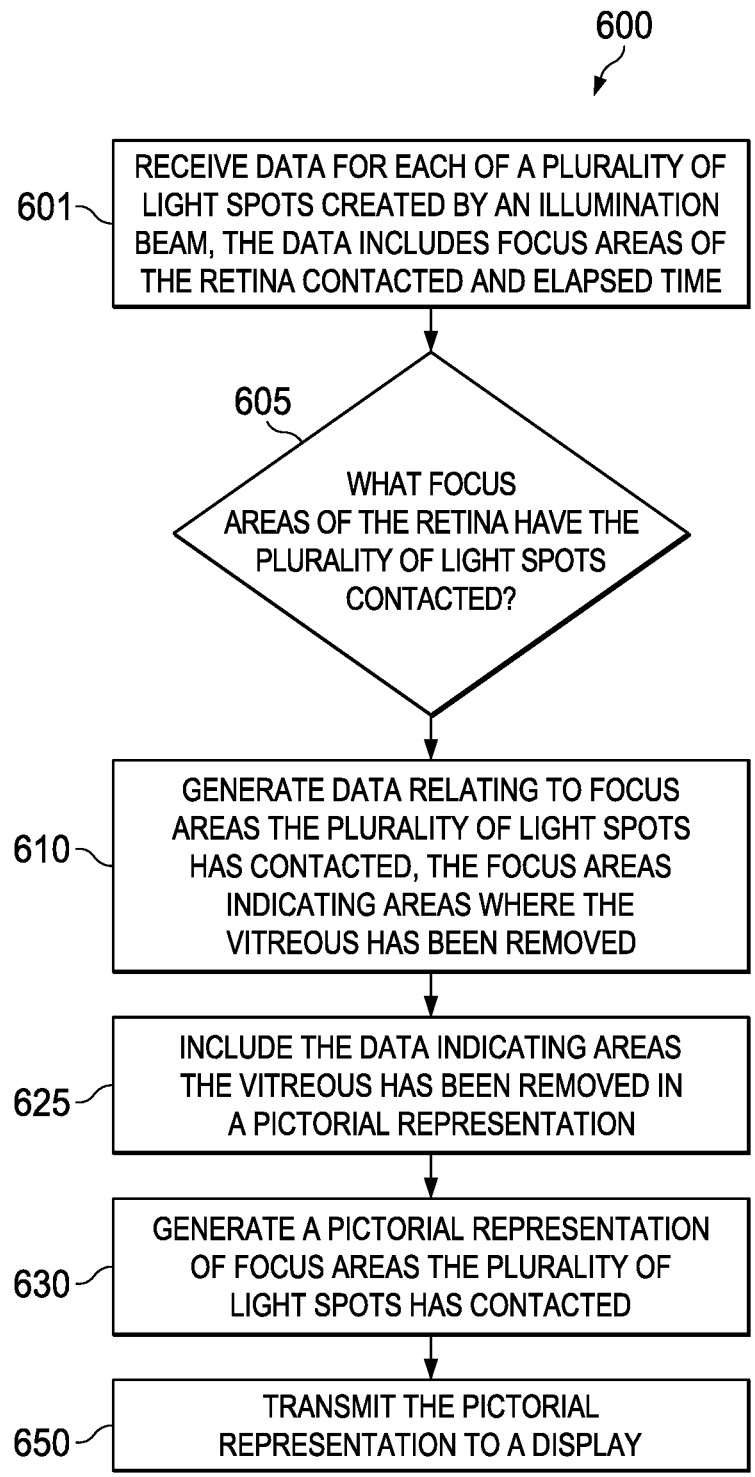
FIG. 6 is a flowchart of a method for determining areas where the vitreous has been removed, based on focus areas contacted by the illumination beam of a vitreous visualization device.

FIG. 6 is a flowchart of a method for determining areas the vitreous has been removed based on focus areas contacted by the illumination beam of a vitreous visualization device. At step 601, data may be received for each of a plurality of light spots created by an illumination beam, such data including focus areas of the retina contacted by the each of the light spots of the plurality and elapsed time the illumination beam has been focused on each focus area. At step 605, the focus areas that the plurality of light spots has contacted may be determined. These focus areas indicate areas where the vitreous has been removed because each light spot is created by the illumination beam, which passes through the cutter port of the VVD, and thus corresponds to areas where the cutter has cut and aspirated the vitreous. At 610, data may be generated to include in a pictorial representation, the data relating to focus areas the plurality of light spots has contacted, and the focus areas indicating areas the vitreous has been removed. At 625, the data indicating areas the vitreous has been removed may be included in a pictorial representation generated at step 630. At step 630, a pictorial representation of focus areas the plurality of light spots has contacted may be generated, and at step 650, the pictorial representation may be transmitted to a display. FIG. 3 provides an example of a pictorial representation that includes data relating to areas the vitreous has been removed. Specifically, colored and shaded focus areas 380 indicate areas where the vitreous has been removed. To provide greater detail, focus area 381, for example, is presented as darker than focus area 382. This darker shade signifies that the light spot has been focused on focus area 381 for a greater amount of elapsed time as compared to focus area 382, which may indicate to the user that further cutting and aspiration is required at focus area 381 in comparison to focus area 382.

The method steps illustrated in FIG. 4 may be performed with any of the steps shown in FIGS. 5 and 6, or any combination thereof. Similarly, the method steps of FIGS. 5 and 6 may be performed individually or in combination with any of the steps of FIG. 4. The data relating to each of a plurality of light spots referred to in 405 of FIG. 4, 501 of FIG. 5, and 601 of FIG. 6 may all contain the same data or any combination of the data relating to the plurality described, such that the subsequent steps may be performed using the data received. The pictorial representation generated in 430 of FIG. 4, 530 of FIG. 5, and 630 of FIG. 6 may be the same pictorial representation, and may include any of the elements generated in preceding steps, for example, warning 425, warning 525, and an indication of areas where the vitreous has been removed 625. FIG. 3 provides an example of a pictorial representation generated and transmitted to a display that includes all of the elements generated in FIGS. 4, 5, and 6.

The above disclosed subject matter is to be considered illustrative, and not restrictive, and the appended claims are intended to cover all such modifications, enhancements, and other embodiments which fall within the true spirit and scope of the present disclosure. For example, although the above systems and methods are discussed in the context of monitoring phototoxicity caused by the illumination beam of a VVD, a similar system may be used, to generate data relating to a light spot and generate corresponding warnings, when the light is generated by any illumination device that produces a well-defined spot.

Further, because all light, and thus optical energy, incident on the retina contributes to phototoxicity, similar systems may be configured to account for other illumination sources in addition to the VVD. Although illumination resulting in a well-defined spot is typically easier to track, similar systems may be configured to account for more diffuse light patterns of other illuminated tools that may be used in conjunction with the VVD. For example, a similar system may model or reference data relating to the typical exposure from such other illuminated tools and integrate this additional exposure into the calculated exposure for each tracked light spot. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for monitoring phototoxicity during ophthalmic surgery comprising:
   a vitreous visualization device connected to an optical fiber operable to propagate an illumination beam, the illumination beam creating a light spot on a retina;
   a surgical microscope;
   a digital camera operable to detect the light spot and generate data relating to the light spot; and
   a processor operable to:
   receive the data from the digital camera relating to the light spot, the data including a size of the light spot and an elapsed time the light spot has been focused on a focus area of the retina;
   determine an amount of optical energy incident on the focus area, the amount of optical energy corresponding to the elapsed time;
   determine a cumulative amount of optical energy incident on the retina, based on the amounts of optical energy incident on a plurality of focus areas;
   determine whether the cumulative amount of optical energy meets or exceeds a warning threshold, defined in relation to a maximum exposure limit for phototoxicity;
   generate a warning when the cumulative amount of optical energy meets or exceeds the warning threshold; and
   transmit the warning to a warning system.

2. The system of claim 1, further comprising a control device connected to the vitreous visualization device, the control device operable to adjust an intensity of the illumination beam, and wherein the processor is further configured to generate and transmit a control signal to the control device, the control signal operable to pause or turn off the illumination beam, when the warning is generated.

3. The system of claim 1, further comprising a control device connected to the vitreous visualization device, the control device operable to adjust an intensity of the illumination beam, and wherein the processor is further configured to generate and transmit a control signal to the control device, the control signal operable to adjust an intensity of the illumination beam, when the warning is generated.

4. The system of claim 3, wherein the processor is further configured to require receipt of a manual confirmation input before adjusting the intensity of the illumination beam.

5. The system of claim 4, further comprising a device for manual confirmation, the device for manual confirmation operable to input a confirmation of an adjustment of intensity of the illumination beam.

6. The system of claim 5, wherein the device for manual confirmation of an adjustment is a button, a switch, a key or a joystick, or any combination thereof.

7. The system of claim 1, wherein the warning system comprises a display operable to present a pictorial representation, and wherein
   the processor is further configured to generate the pictorial representation to indicate the warning generated, when the warning is generated.

8. The system of claim 7, wherein the pictorial representation further indicates a cumulative amount of optical energy incident on each focus area of the retina.

9. The system of claim 7, wherein the pictorial representation further indicates an increase in optical energy incident on each focus area of the retina.

10. The system of claim 1, wherein the processor is further configured to determine a distance between a cutter on the vitreous visualization device and the retina, the distance determined in relation to the size of the light spot on the retina.

11. The system of claim 10, wherein the processor is further configured to determine whether the distance between the cutter and the retina meets or exceeds a distance threshold.

12. The system of claim 11, wherein the processor is further configured to generate the warning when the distance meets or exceeds a distance threshold.

13. The system of claim 7, wherein the pictorial representation further indicates a change in the size of the light spot, the change corresponding to a new distance between the cutter and the retina.

14. The system of claim 1, wherein the processor is further configured to:
    determine focus areas of the retina that the light spot has contacted; and
    generate data relating to focus areas that the light spot has contacted, the focus areas indicating that areas where the vitreous has been removed.

15. The system of claim 7, wherein the pictorial representation further indicates areas where the vitreous has been removed.

* * * * *